United States Patent
Alfano et al.

(10) Patent No.: US 10,962,751 B2
(45) Date of Patent: Mar. 30, 2021

(54) SUPERCONTINUUM MICROSCOPE FOR RESONANCE AND NON-RESONANCE ENHANCED LINEAR AND NONLINEAR IMAGES AND TIME RESOLVED MICROSCOPE FOR TISSUES AND MATERIALS

(71) Applicants: Robert Alfano, New York, NY (US); Lingyan Shi, New York, NY (US)

(72) Inventors: Robert Alfano, New York, NY (US); Lingyan Shi, New York, NY (US)

(73) Assignee: Robert Alfano, New York, NY (US), part interest ( * ) Notice: Subject to any disclaimer, the term of this patent is extended or adjusted under 35 U.S.C. 154(b) by 775 days.

(21) Appl. No.: 15/409,303

(22) Filed: Jan. 18, 2017

(65) Prior Publication Data

US 2017/0153435 A1 Jun. 1, 2017

Related U.S. Application Data

(60) Continuation of application No. 14/996,449, filed on Jan. 15, 2016, now Pat. No. 9,561,077, and a division
(Continued)

(51) Int. Cl.
*G02B 21/00* (2006.01)
*G06N 10/00* (2019.01)
(Continued)

(52) U.S. Cl.
CPC .......... *G02B 21/0064* (2013.01); *A61B 18/20* (2013.01); *A61N 5/0622* (2013.01);
(Continued)

(58) Field of Classification Search
CPC combination set(s) only.
See application file for complete search history.

(56) References Cited

U.S. PATENT DOCUMENTS

| 4,288,528 A | 9/1981 | Picquendar et al. |
| 5,532,873 A | 7/1996 | Dixon |

(Continued)

OTHER PUBLICATIONS

R. R. Alfano et al., PRL, 24, 592-594, 584-587, 1217-1220, (1970).
(Continued)

*Primary Examiner* — Joseph M Santos Rodriguez
(74) *Attorney, Agent, or Firm* — Nolte Lackenbach Siegel; Myron Greenspan

(57) ABSTRACT

Supercontinuum (SC) (~400 nm to ~2500 nm) and a microscope produce enhanced microscopic images on sub-micron to cm scale of linear ($\chi_1$) and nonlinear ($\chi_2$, $\chi_3$, $\chi_4$ ...) processes via resonance including linear absorption, SHG, THG, SRG, SRL, SRS, 2PEF, 3PEF, 4PEF, and inverse Raman in a microscope for 2D and 3D imaging. Images and processes in 2D and 3D arise from electronic and vibrational resonances transitions in biological and medical tissues, cells, condensed matter applications. Resonant Stimulated Raman Scattering (RSRS) is proposed to improve vibrational imaging of biomaterials by using part of SC. Quantum mechanical processes from SC for 2 and 4 photons to improve resolution and imaging using entangled photons are described. The addition of time measuring instrument like a Streak camera and the scattering coefficient $\mu_s'$ can be mapped to create images of tissue and biomaterial in 5D: Space (3D), Time, and Wavelength.

2 Claims, 8 Drawing Sheets

Related U.S. Application Data of application No. 12/723,091, filed on Mar. 12, 2010, now Pat. No. 9,414,887.

(51) Int. Cl.

| | |
|---|---|
| *A61B 18/20* | (2006.01) |
| *A61N 5/06* | (2006.01) |
| *G01N 33/483* | (2006.01) |
| *G02F 1/35* | (2006.01) |
| *G02F 1/355* | (2006.01) |
| *G02F 1/365* | (2006.01) |
| *A61B 5/00* | (2006.01) |
| *A61B 17/00* | (2006.01) |
| *A61B 18/18* | (2006.01) |
| *A61N 5/067* | (2006.01) |

(52) U.S. Cl.
CPC ..... *G01N 33/4833* (2013.01); *G02B 21/0032* (2013.01); *G02B 21/0084* (2013.01); *G02F 1/3515* (2013.01); *G02F 1/3536* (2013.01); *G02F 1/3551* (2013.01); *G02F 1/365* (2013.01); *G06N 10/00* (2019.01); *A61B 5/0066* (2013.01); *A61B 2017/00508* (2013.01); *A61B 2018/1807* (2013.01); *A61B 2018/2065* (2013.01); *A61N 2005/067* (2013.01); *A61N 2005/0659* (2013.01); *G02F 1/355* (2013.01); *G02F 2001/3528* (2013.01)

(56) References Cited

U.S. PATENT DOCUMENTS

| | | | |
|---|---|---|---|
| 6,450,949 B1 | 9/2002 | Farkas et al. | |
| 8,641,193 B2 * | 2/2014 | Jiao | A61B 3/1241 351/206 |
| 2006/0291042 A1 | 12/2006 | Alfano et al. | |
| 2008/0088849 A1 * | 4/2008 | De Lega | G01B 9/02044 356/450 |
| 2009/0073432 A1 * | 3/2009 | Jalali | G01N 21/636 356/301 |
| 2009/0097512 A1 * | 4/2009 | Clowes | G02B 21/16 372/21 |
| 2013/0338479 A1 * | 12/2013 | Pogue | A61B 5/0059 600/408 |

OTHER PUBLICATIONS

See, K. J. Ranka et al., Opt. Lett. 25, 25 (2000), and S. Coen, Chau, Leonhardt, and J. Harvey, Josa B, 26, 753 (2002).
P. B. Corkum et al., PRL, 57, 2268 (1986).
Lehmeier et al., Opt. Comm., 56, 67-72 (1985).

* cited by examiner $$\overline{K}_L + \overline{K}_L = \overline{K}_S + \overline{K}_A$$

SUPERCONTINUUM MICROSCOPE FOR RESONANCE AND NON-RESONANCE ENHANCED LINEAR AND NONLINEAR IMAGES AND TIME RESOLVED MICROSCOPE FOR TISSUES AND MATERIALS

BACKGROUND OF THE INVENTION

1. Field of the Invention

The present invention relates generally to Supercontinuum (SC) light generated for use in microscopes to create a SC microscope apparatus for medical, condensed matter and biological applications for spectral imaging tissues and materials; a time resolved microscope for scattering transport length; and 4 wave non-linear optics (NLO) to create entangled photons for improved imaging with higher resolution remotely. The aims are to produce SC optical, NIR and SWIR microscopes for deeper imaging into materials using the spectral and time. Images up to 5D tomography may be obtained to form the ultimate images of material and tissue by adding time and wavelength λ to space to get [xyz, t, λ] maps.

2. Description of the Related Art

The versatility of light is a direct result of the many forms it is able to take, for example, brief flashes, focused spots, broad continuous beams, dim or intense light, low- or high-frequency light, and light containing many frequencies at once without light we could not see. The frequency of visible light determines its color, and is related to the light's wavelength, i.e., shorter wavelengths correspond to higher frequencies. There are other salient properties of light: polarization, coherence, and speed. Light in the form of photons makes quantum mechanical processes as transitions among energy levels in materials to get excited, and under special situation can be coupled together in twins and even multiple photons in 2, 3 or 4 correlated to share information being entangled. The use of the time resolved aspect of SC to achieve imaging in turbid medium the key tissues light scattering coefficients ($\mu_s'$, $\mu_s$) and absorption coefficients ($\mu_a$) spatially in 2D and 3D maps and at different wavelengths of the SC or other ultrafast laser source with pulse duration <10 ps from the temporal scatter profile from points (xy) and z in the tissue in transmission and backscatter images methods. The SC time resolved microscope uses the temporal profile of the ballistic and diffusive shape aspects in time to image the key characteristics properties in material and tissue at depths.

An incandescent bulb or LEDs emits light across a full visible spectrum, resulting in white light. However, light from an incandescent bulb and LEDs has several drawbacks. Specifically, this type of light has a relatively low intensity and brightness, and it is neither coherent nor collimated in a single direction. Therefore, the individual light particles, or photons, do not oscillate in phase with one another. By contrast, lasers do not have the above-mentioned drawbacks that result from light of an incandescent bulb or LEDs. Instead of emitting white light, a laser emits a narrow band of frequencies, resulting in light of a specific color. For many applications, coherent light at a single frequency, or a narrow band of frequencies, is more than adequate. However, having a light source, such as the SC that combines the properties of a laser with short pulses, coherence, and those of a broad bandwidth incandescent bulb, provides for a new realm of applications for medical, communication, quantum effects, imaging and information.

Seminal work on the SC's generation was performed when it was discovered in 1970 [1]. 100 MegaWatt (MW), 10 picosecond (ps) pulses were focused into condensed materials in order to produce the SC with a white light continuum of colors, see patent 1974 with first application in [2] and most recently updated in 2016 [3]. The SC light can be generated over a frequency octave using microstructure fibers, holey filters, and photonic crystal fibers, and using modest energies of <100 femtosecond (fs) ps lasers. Using kilowatt peak power fs pulses, SC spans from 400 to 1600 nanometers (nm) can be generated in photonic crystal fibers. For example, 1 meter of NonLinear-Polarization Maintaining (NL-PM) 750 photonic crystal fiber made by Crystal Fibre Corp. can produce more than an octave, i.e., 1200 nm bandwidth using 800 nm 50 fs-67 milliWatt (mW) average power from a Ti-sapphire laser. The broad SC spectrum results from NLO process of Self-Phase Modulation (SPM), 4 Wave Mixing (4WM), and stimulated Raman and Soliton generation. Thus, the SC light can be generated on a spectrum greater than an octave, where 500 to 1000 nm is an octave, and a two octave SC spans from 400 to 1600 nm. The SC intensity can be >1 GW/cm$^2$ nm to produce for nonlinear effects in medical, condensed matter and atomic physics and investigate Resonance effect in both electronic and vibration states such as [2] where absorption at vibrations is in anti-Stokes part of pump laser for SC. This [2] anti-Stokes presents the physics to produce a inverse stimulated Raman microscope—loss in anti-Stokes part of SC.

A SC beam [3] can be produced by focusing ~350 microjoule (μJ) 70 fs pulses from Ti-sapphire laser systems into a long metallic cylinder of 90 centimeters (cm), which contains rare gases, such as Argon (Ar), Krypton (Kr) and Xenon (Xe), at modest pressures from 2 to 30 Atmospheres (atm). A milliJoule (mJ), which is the energy required to lift a paper clip several centimeters against the earth's gravity, may appear to be a small amount of energy. However, when a mJ to μJ pulse propagates in microscope optics it may broadens to about 10 ps. The SC produces into a ps and focuses into a tight spot it represents a GigaWatt (GW) of power and an extremely high intensity. With this high intensity, the pulses can propagate through a few centimeters (cm) of glass, inducing a Kerr effect strong enough to spread the pulses' bandwidth considerably even in the short time that they passed through the glass by distortion of the electron clouds in the material.

Fibers that add the length from 5 cm to 5 meters and can be used for SC generation are known as microstructure fibers. A cross section of such fibers reveals a pattern of holes that runs continuously through the entire length of the fibers. In one commonly used design, the pattern of holes surrounds a solid silica core, similar to a honeycomb with only the central hole filled. The core has a high index of refraction, whereas the surrounding cladding, with its air holes interspersed with silica, has a lower refraction index. The concentric arrangement of refractive indices serves to guide the light pulses along the fiber. The use of these fibers with zero and anomalous dispersion has enabled the generation of the SC light extending more than two octaves from InfraRed (IR) to UltraViolet (UV). The placement of the zero dispersion point in the fibers in blue and Near InfraRed (NIR) will produce pulses covering UV, visible, and NIR regions from 300 nm to 2500 nm. SC can be generated into MIR using special fibers and semiconductors.

The generation of the SC light in optical fibers has unleashed a world wide range of studies and diverse applications. One of the most important and mature of these applications is the development of extremely accurate frequency measurements and clocks. The SC light is useful in optical frequency comb techniques, which enable improved accuracy with simpler and smaller systems. Specifically, self-referencing becomes possible when the frequency comb extends across a full octave. In this approach, the frequency of light is doubled at the low-frequency end of the spectrum and is used to interfere with light at the high-frequency end.

Researchers are now striving to develop systems capable of measuring frequencies to a fractional accuracy of $10^{-16}$ to $10^{-18}$. Such extreme accuracy would have practical implications for improvements in Global Positioning Systems, space navigation, and the alignment of very large arrays of radio telescopes. The systems would also be utilized in tests of special relativity and related fundamental principles such as the isotropy of space, the symmetry of matter and antimatter, and the constancy of the constants of nature.

Frequency measurements and clocks are two facets of the same technology. Ultimately, the optical frequency comb might enable fractional accuracies of $10^{-18}$, which would be ideal for timing in optical computers and even for detecting oil and mineral deposits by their minute effects on the nearby gravitational field. The SC light is also enabling technology to produce shorter pulses into attosecond ($10^{-18}$ sec) and zeptosecond ($10^{-21}$ sec) regions.

An application with more immediate commercial implications than ultra-precise frequency measurements is telecommunications. Several of the SC's key properties make it an ideal basis for telecommunication systems that are capable of transmitting data more than 1,000 times faster than present-day systems for terabits into pentabits. Optical fiber carrying IR light is already the most widely used means of sending data at high rates over long distances. In an effort to keep up with the ever-increasing worldwide demand for larger-capacity communications systems and networks, there is a need to include more data into a fiber. The goal is to achieve transmission rates of terabits ($10^{12}$) and pentabits ($10^{15}$) per second. Typical fiber-optic systems currently transmit data between cities at about 10 gigabits per second, or 0.01 terabit per second.

The ultrabroad bandwidth of the SC light makes it a cost-effective way to obtain numerous wavelength channels without having to use hundreds of lasers. That bandwidth could be utilized in superdense wavelength division multiplexing, in which data streams are encoded onto many different wavelengths of light that are transmitted simultaneously. The SC, unlike the light from 100 individual lasers, can be coherent across a wide range of frequencies, which aids in the degree of control that can be brought to bear on the light.

SC combines with spatial modes from Vector Vortex light will produce more information beyond the pentabits into exabits and zettabits. Alternatively, a series of ultrashort pulses of the SC light (shorter than 100 fs, or $10^{-13}$ second) can be sent, with sequences representing different data channels interleaved with one another, referred to as Time-Division Multiplexing (TDM). With short pulses, it is important to be able to control the precise relation between the individual oscillations of the electric field (the carrier wave) and the pulse envelope. This property, referred to as the relative phase of the carrier and the envelope, determines, for example, whether the peak of the pulse envelope occurs at an instant when the electric field of the wave is at a peak or a trough, or somewhere in between. The properties of the SC light facilitate such control.

Data transmission rates of terabits/second have already been achieved using a small segment of the SC light spectrum. However, many challenges remain in order to improve the speed and achieve petabit/second operation and beyond into exabits. These challenges include reducing the duration of a bit to about a ps and increasing the number of coherent wavelengths in the SC.

The telecommunication applications rely on producing the SC light in the completely controlled environment of an optical fiber; however, for some applications the SC light is generated in open air. One such application is the remote sensing of molecular species present in air. When intense ultrafast laser pulses travel through the air, they can produce long, narrow "filaments" in which the air is ionized. Within those filaments electrons are knocked off the air's molecules forming a plasma of positive ions and negatively charged electrons. These filaments can guide the light pulses and keep them from spreading, a process that scientists attribute to a balance between defocusing caused by diffraction (the tendency for a wave to spread out from a small aperture) and self-focusing caused by the ionized plasma.

Within the filaments a significant amount of the pulses' power can convert to SC white light over distances greater than 20 meters. Pollutants and aerosols in the air will absorb the light at characteristic frequencies, and the broad spectrum of the SC light enables one to detect their absorption spectra simultaneously in the UV, visible and IR bands.

In addition to probing the air around us, the SC light is useful in producing high-resolution images of tissues within body. Optical Coherence Tomography (OCT) can be carried out in situ in living organisms as a diagnostic tool to measure tissue layers. To produce an OCT image, a light is split into two parts. A first part of the light illuminates a spot in the sample, whereas a second part, or a reference light, enters a length of fiber. When the reference light recombines with light that the sample reflected or scattered, the two interfere strongly, provided that they each spent the same length of time on their respective journeys. High-resolution OCT imaging relies on a short coherence length of the source light, which requires a very accurate timing match.

Thus, when the spot of light penetrates into the sample, only light coming back from one specific depth will interfere with the reference light. Scanning the light laterally across the sample while keeping the travel time of the reference light fixed thereby produces a two-dimensional image of the sample at a certain depth. The thickness of the layer that contributes to the image is called the axial resolution of the image.

Early OCT imaging systems relied on a type of diode to provide the light and had an axial resolution of 10 to 15 microns. The axial resolution also depends on the bandwidth of the light source. A broader bandwidth enables finer resolution. The SC light has a short coherence length and a bandwidth broader than any fs laser, making it ideal for high-resolution OCT imaging. The SC light generated in microstructured fibers has been used to produce images of cells with an axial resolution of 0.5 micron. Using single photons from SC produces quantum optical tomography microscope and more intense 4 wave coupled in angular pattern SC, see FIG. 1.

Light is also capable of photo-activating molecular components within tissue (in the matrix and/or cells) in order to fuse a cut together with minimal scarring using the water absorption from overtone and combination vibrational bonds at 1450 nm, spanning from 1000 to 1600 nm. Tissue welding can be achieved using lasers, such as tunable $Cr^{4+}$ lasers, semiconductor lasers, and fiber lasers, where the weld strength follows the absorption spectrum of water. Tissue wounds, bruises, and burns can be healed using laser and lamp light covering UV to visible regions at an average irradiance of ~100 mW/cm$^2$. Microsecond pulsed lasers from 1850 nm to 2100 nm may be used to stimulate nerves, and to kill bacteria and viruses by exciting upper UV states with UV and blue light transitions.

SC has 4 photons mixing FIGS. 1 and 2 which are entangled for remote imaging at different locations in quantum optical imaging for imaging inside tissues and cells.

There is a need for a universal light source for microscopy using linear and nonlinear optics with resonance and non-resonance transition to unravel the fundamental processes in tissues, cells and materials by optical imaging on small scale.

The SC Time microscope can create 5D tomography images: space, time, wavelength a [xyz, t, and $\lambda$—(r,t,$\lambda$)]. In time resolved microscope the transport scattering length (Ltr) at xy position at z for given wavelength $\lambda$ of SC for an image map of tissue obtained from I(t) scattered profile in time.

SUMMARY OF THE INVENTION

The present invention is directed to a microscope system used with SC to form a SC microscope for tissues, cells and materials with high resolution imaging. The SC light source with unique Temporal and Spectral properties is used to image and enhance linear and nonlinear processes in resonance from electronic singlet states Sn and triplet states Tn and vibrational states under a microscope for 2D and 3D display of structure in tissues, smears (PAP) and cells in animals and humans on sub-micron to cm scale. Images up to 5-D may be obtained to form the ultimate images of material by adding time and wavelength $\lambda$: [xyz,t,$\lambda$] using SC and streak camera with microscope and scanning.

BRIEF DESCRIPTION OF THE DRAWINGS

The above and other aspects, features and advantages of the present invention will be more apparent from the following description when taken in conjunction with the accompanying drawings, in which.

DETAILED DESCRIPTION

Four Photon Entanglement Quantum Imaging for Deep Imaging

Figure 1:
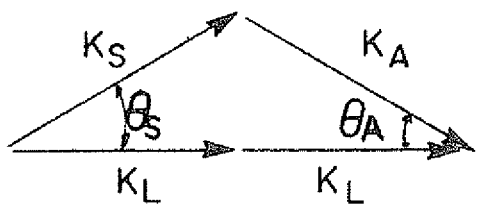
FIG. 1 illustrates Four (4)-Wave phase K matching triangle.
Figure 2:
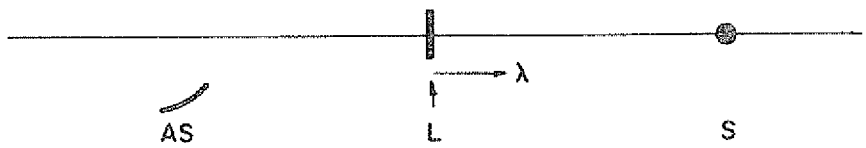
FIG. 2 illustrates angular phase matching showing 4 photons coupling (2 Laser and Stokes and Anti-Stokes) angular emission vs wavelengths of the entangle 4 photons.
Figure 2:
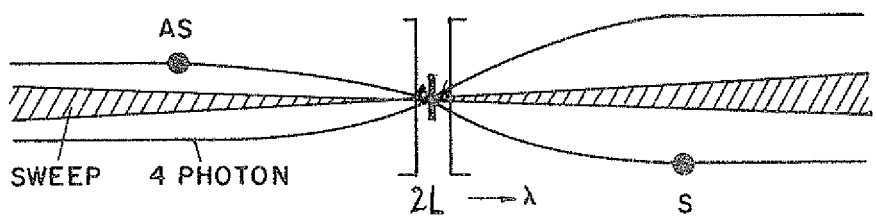

The generation of light over the visible region in an angular pattern is another striking nonlinear optical effect observed when intense 532 nm picosecond laser pulses are passed through materials at different angles. This angular emission [FIGS. 1 and 2] is shown to result from the coupling of four photons via the nonlinear coefficient $n_2(\chi^3)$ to be entangled.

This 4-wave process has been called four-photon parametric amplification or light by light scattering for quantum optical microscope for nm scale.

Entanglement of 2 or more photons is based on quantum mechanisms and forms ways of different quantum information methods and imaging. Two photons are typically used on photon level requiring long processing and averaging times. The need for high intensity photon approach of coupled entangled photons using higher correlated photons is needed. Here we propose 4 wave approach from $\chi_3$ in angular and collinear generator arrangement. The coupled twins of Stokes and antiStokes with 2 pump and 2 laser photons are entangled at well defined angle of high photon levels to be used for various quantum information protocols such as cryptography and computation, loudly and non loudly in microscope or free space. Signal averaging times are reduced of 4-photon coupling.

Figure 3:
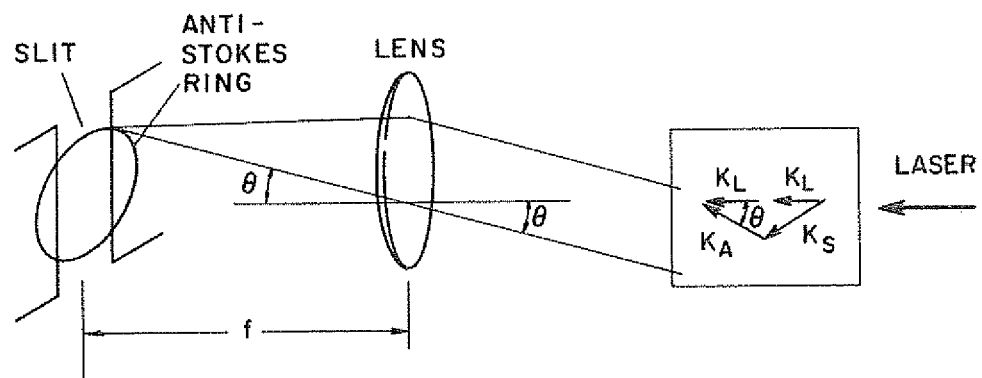
FIG. 3 illustrates the angular emission 4 photon ring on slit of spectrometer.

Nondegenerate four-photon stimulated emission ($\omega_1 \neq \omega_2 \neq \omega_3 \neq \omega_4$) in many materials originating from scale filaments created under high power 530 nm picosecond-pulse excitation [1]. The four-photon coupling process originates through the distortion of the atomic configuration inside the filaments in the materials. Positive and negative SPM frequency components are generated inside the filaments. The frequency-swept photons and laser photons are coupled to the laser field via the third-order susceptibility $\chi^3$ or the intensity-dependent dielectric refractive index coefficient $n_2$. The four-photon process is of the type $\vec{K}_L + \vec{K}_L = \vec{K}_A + \vec{K}_S$ schematically depicted in FIG. 1 where $\vec{K}_L$, $\vec{K}_A$, $\vec{K}_S$ are the wave vectors of the laser beam, Stokes-shifted photons, and anti-Stokes-shifted photons, respectively. The maximum amplification of the weak waves occurs along an angular direction governed by phase match among the four photons (See FIG. 2 and FIG. 3). These four photons (2 laser, Stokes, and anti-Stokes) are entangled over large number of wavelengths and angles in 4 wave triangle (FIG. 1) show 4 photons entanglement (2$\omega$L, $\omega$s and $\omega$as). These 4 correlated photons form a new imaging tool for entangle images with intense beam of entangled photons.

Resonance Linear and Nonlinear Effects

There are no teachings on the use of SC source microscope applications for resonant effects in linear, SHG, THG, FHG (Fourth Harmonic generation), SRS (Stimulated Raman Scattering), 2PEF (2 Photon Excitation Fluorescence), 3PEF (3 Photon Excitation Fluorescence), 4PEF (4 Photon Excitation Fluorescence), and inverse Raman effect where frequencies in SC make transitions to electronic and vibrational states. Background theory for resonant and non-resonant SC can be used to enhance linear and non-linear optical effects via susceptibilities $\chi_1$, $\chi_2$, $\chi_3$, and $\chi_4$ when frequencies are close to transitions for enhanced microscope images. In the past non electronic resonant process for pumping and probing beams were used for imaging, such as CARS, SRS, and Multi photons in $\chi_1$, $\chi_2$, $\chi_3$, and $\chi_4$.

Figure 4:
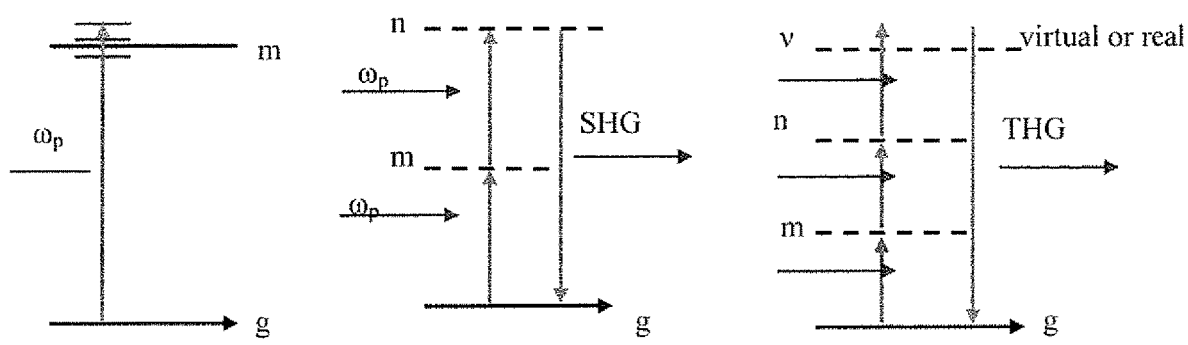
FIG. 4 illustrates linear and nonlinear optical effect second harmonic generation (SHG) and third harmonic generation (THG) processes energy level diagrams.
Figure 5:
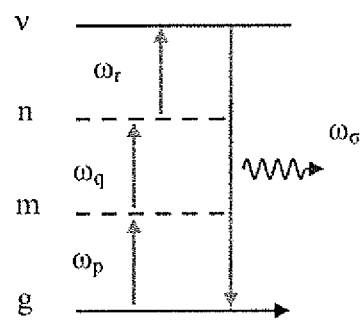
FIG. 5 illustrates enhanced three photon emission in real states (v=real state)

SC can be used to probe enhanced linear and non-linear effects via the denominators in quantum mechanical description of $\chi$'s via polarization P. Linear and nonlinear optical effect processes energy level diagrams are shown in FIG. 4 and FIG. 5.

The polarization P is expanded in series of E, electric field of laser:

$$P = \chi_1 E + \chi_2 E^2 + \chi_3 E^3 + \chi_4 E^4 + \quad (1)$$

The susceptibilities $\chi_1, \chi_2, \chi_3, \chi_4 \ldots$ give size of optical effect, with the resonances appear in denominators for electronic and vibrational states. The SC covers resonance process for imaging.

Using Quantum Mechanics Perturbation Theory:
Linear Effects
$\chi^1$ between ground g and excited states m:

$$\chi^1(\omega_p) = \sum_m \frac{\mu_{gm}\mu_{mg}}{\omega_{mg} - \omega_p}, \quad (2)$$

where $\omega_{mg} = \omega_{mg}^\circ - e\Gamma_m$, $\mu$ is dipole moment, and $\omega_p$ is light frequency in SC. When $\omega_{mg}^\circ = \omega_p$ there is a resonance, $\chi^1$ is large and there is absorption.

Second Order Effects
$\chi^2$—such as SHG imaging. The equation $\chi^2$ is:

$$\chi^2(\omega_p, \omega_q) = \sum_{mn} \frac{\mu_{gn}\mu_{nm}\mu_{mg}}{(\omega_{ng} - \omega_p - \omega_q)(\omega_{mg} - \omega_p)}, \quad (3)$$

where $\omega = \omega_p + \omega_q$ e, $\mu_{ng}$ is dipole transition between grand g and excited state n (real or virtual).

For SHG $\omega = \omega_p + \omega_q = 2\omega_q$ if p=q. When $\omega_p, \omega_q, \omega_{p+q}$ match a real state, $\omega_{mg}^\circ$ or $\omega_{ng}^\circ$, the denominator get small and close to 0 and $\chi^2$ get large and SHG increases, say for collagen $\omega_{ng} \sim 340$ nm, flavins $\omega_{ng} \sim 440$ nm, and Tryptophan $\omega_{ng} \sim 290$ nm, where $$\omega_{ng} = \omega_{ng}^0 - i\frac{\Gamma_m}{2}.$$

The SC spectra for $\chi^2$ SHG can tell which molecule is activated, such as collagen, Flavin, Carotene, and others in skin and brain tissue. For SHG:

$$\chi^2(\omega_p, \omega_q) = \sum_{mn} \frac{\mu_{gn}\mu_{nm}\mu_{mg}}{(\omega_{ng} - 2\omega_p)(\omega_{mg} - \omega_p)}, \quad (4)$$

SHG resonance for real states at $\omega_{ng} = 2\omega_{qp}$ in the SC for highlight regions in sample images under microscope.

Third Order Effects
$\chi^3$ is THG microscopy, 2PEF, and SRS. $\chi^3$ is written in 4 terms:

$$\chi^3(\omega_\sigma, \omega_r, \omega_p, \omega_q) \sim \sum_{mnv} \frac{\mu_{gv}\mu_{vn}\mu_{nm}\mu_{ng}}{(\omega_{vg} - \omega_\sigma)(\omega_{ng} - \omega_q - \omega_p)(\omega_{ng} - \omega_p)}, + \quad (5)$$

where $\omega_{eg} = \omega_{eg}^0 - i\frac{\Gamma_i}{2}$, $\mu_{eg}$ is dipole transition between i and g states and $\omega_o = \omega_p + \omega_q + \omega_r$ pumps. For $\omega_p = \omega_q = \omega_o$, $\omega_v = \omega_{3\omega_p}$ is THG term where $\omega_p$ is pump portion of SC. So, when $\omega_{vq} = 3\omega_p = \omega_{vq}^\circ$ then THG is enhanced in FIG. 5 in real states $$\omega_{vq} = \omega_{vq}^0 - i\frac{\Gamma_v}{2} = \omega_\sigma \quad (6)$$

Figure 6:
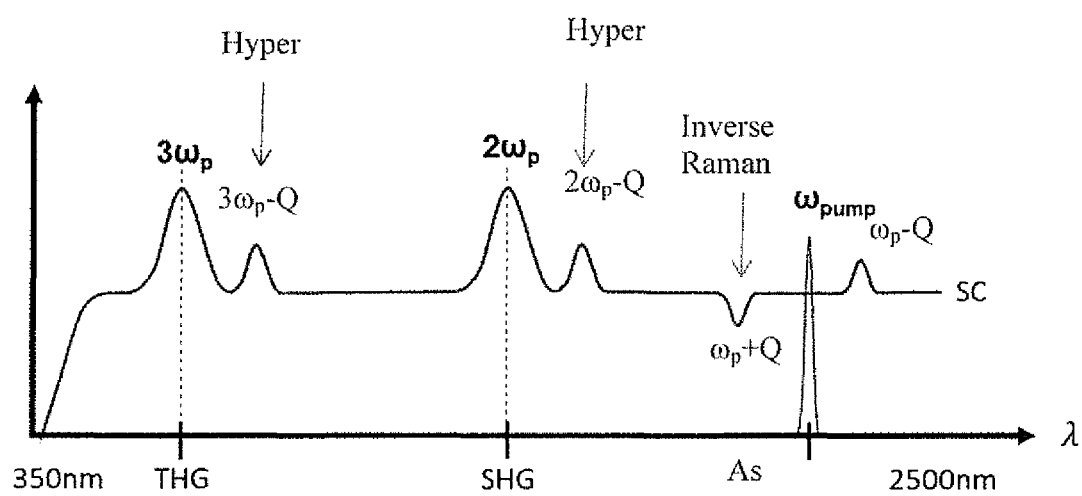
FIG. 6 illustrates intensity of SC for NLO resonance and non-resonances at second harmonic (SH), third harmonic (TH), Stimulated Raman, hyper-stimulated Raman. (2 photon), and (3 photon), Inverse Raman.

Using SC there are resonance in real states, there will be enhance at SHG and THG to determine the type of 2P and 3P images in tissues, see FIG. 6 for resonant and non-resonant flat background. There may be peaks from Hyper Raman ($2^{nd}$ and $3^{rd}$ order) and Hyper Rayleigh ($2^{nd}$ and $3^{rd}$ orders) process from vibrations and index of refraction. There may be absorption in SC from excited state transitions in singlet Sn and triple Tn states NLO absorptions and absorption at antiStokes from vibrations in a sample to images as loss of SC at vibrations due to Inverse Raman events [2]. There may resonances from electronic states to enhance vibrational states for Resonant Stimulated Raman Scattering (RSRS) effect.

Examples for images from key molecules of tissues, cells and smears from brain, breast, cervix and other cancers for:
SHG collagen (380 nm)+SC (760 nm)=SHG–380 nm increase ($\chi^2$)
THG Tryptophan (296 nm)+SC (800 nm)=THG–296 nm increase ($\chi^3$)
3 photon excitation fluorescence (3PEF) Tryptophan+SC=800 nm to 850 pump emission 340 nm; and
2 photon excitation fluorescence (2PEF) Flavins+SC=500 nm emission ($\chi^3$)
Inverse Raman in SC from $CH_3$ (Carbon-H Bond) and $CH_2$ (Carbon-H Bond) from lipids and proteins in tissue sample.
RSRS from Flavins and carotene from singlet states enhance SR Loss and Gain imaging.

Narrow-band (NB) and wide band (WB) filters are used to select pumping zones for enhanced signal images of molecules in tissues and cells in selected spectral areas of SC in FIG. 6.

Figure 7:
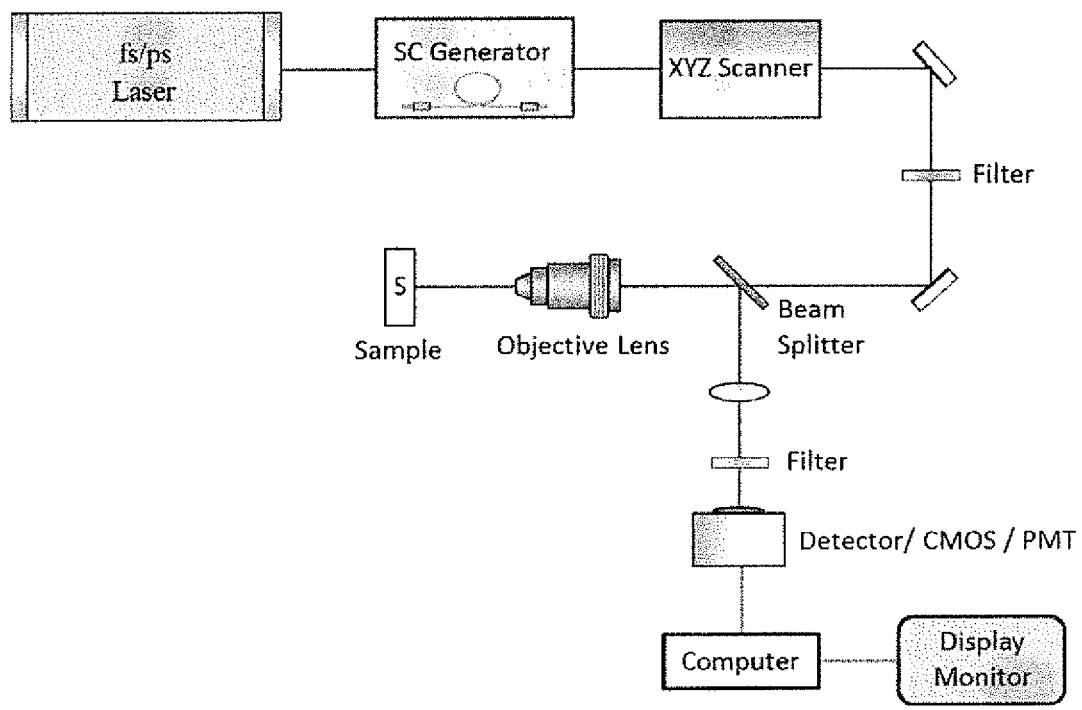
FIG. 7 illustrates an SC microscope apparatus (major components) in accordance to the invention.
Figure 8:
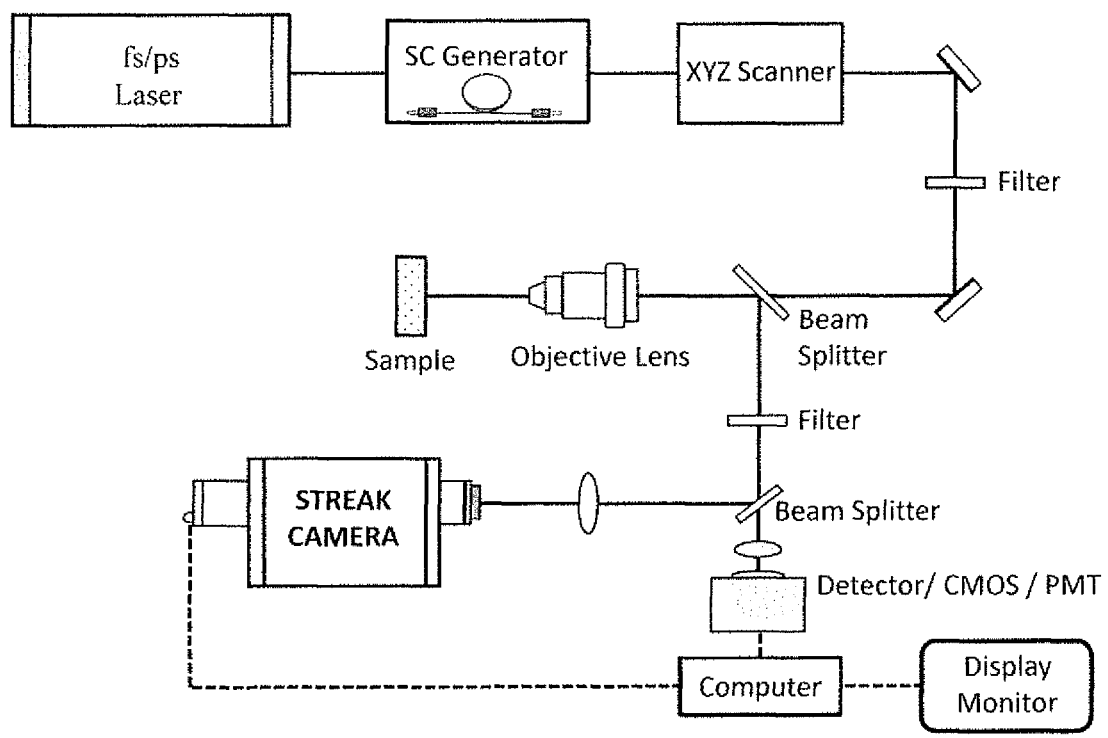
FIG. 8 illustrates a time resolved SC streak camera microscope system combined with spectral imaging.

When the pump in SC matches real states at frequency in materials—solids, liquids, tissues and cells, chemical and/or condensed matter of microscope images, a 10× to 100× objectives are used. The invention provides a new ultrahigh resolution imaging method and device to use SC light as source in a microscope for medical, biological, and condensed matter to determine which molecule types are in resonance from SC spectrum. The major components of the SC microscope apparatus are shown in FIG. 7. The invention teaches the coupling a SC with optical microscope to obtain 2D and 3D images of molecule fingerprints for SHG, THG, 2PEF, 3PEF and linear absorption images of cells and inside cells for DNA and RNA and components inside cells using $\chi_1, \chi_2, \chi_3, \chi_4$ processes. Resonances are from electronic and vibrational states. The inverse anti stokes Raman will yield loss in the continuum at Raman AntiStokes wavelength from pump spectral line to give absorption images at vibration Raman lines in material: solids, liquids, tissue and biomedical media cells and smears.

The SC microscope shown in FIG. 7 may be used as a pathology approach without using extrinsic dyes and stains but using instead multiphoton SC processes such as Second Harmonic generation (SHG), Third Harmonic generation (THG), 2PEF, 3PEF and SRS Loss and gain imaging of the key native label free molecules like the following: collagen, elastin, NADH, lipids, amino acids, and proteins in tissue and smears.

In the past the gold standard was to use stains and dyes for pathology evaluation such as Eosin H&E, Hematoxylin, and chemical labeling for Histopathology evaluation of tissue slice or smear (PAP) in a clinical lab which took long time on the order of many hours to do. The tissues are fixed using formalin, paraffin embedded requiring many hours on the order of >8 hrs. The delay is not good while the optical SC NLO processes and images take less hour.

The multiple photon SC microscope images with filters can reduce the expense and can analyze fresh unlabeled stain free tissue and smears. Native imaging using SC microscope can give pathology information without staining. The speed increases without the need for tissue preparation using dyes. The image contrast of 2PEF, 3PEF, SHG and THG and Stimulated Raman Scattering (SRS), Stimulated Raman Gain (SRG) and Stimulated Raman Loss (SRL) can be used for giving histopathology information from the images of local structure in the tissue and smears images using non-linear optical methods from selected spectral parts of the SC. These form new microscope clinical tools for evaluating tissue without dyes to stain samples but using an optical pathology SC microscope to image the structure of tissue cells and components inside cells of tissue for cancer and clinical evaluation.

The SC Microscope may be used for vibration state in tissue, cells and material for an ultra-broadband Stimulated Raman Application for chemical, biomarkers molecules in cells and tissues such as $CH_2$ and $CH_3$ vibrations from proteins and lipids about 1600 $cm^{-1}$ and 2900 $cm^{-1}$ and others are possible as would be evident to those skilled in the art.

Resonant Stimulated Raman Scattering Via Anharmonic Interactions SC Microscope

Raman scattering is one of the key optical spectroscopic processes arising from inelastic scattering of light with vibrations in materials. The scattered light has a characteristic frequency shift due to vibrations accompanied by generation of optical phonons in the material. The Raman effect has been an active field of research in various fields of science since its discovery in 1928 by Raman and Krishnan. Spontaneous Raman (SR), despite being the weakest form of scattering, has widely been used as a powerful technique to investigate complex molecular and solid-state systems. Raman investigations exploded in the sixties with the discovery of different types of lasers. The Raman process occurs when a photon is scattered from a vibrational mode having its energy difference from the incident beam by the vibrational frequencies. There are several different types of Raman processes that can occur depending on the types of interactions with laser, such as spontaneous, resonance, and stimulated Raman.

An enhancement of the Raman signal, essential for studies at low concentrations or in low cross section compounds, is achieved by Resonant Raman Spectroscopy (RRS), in which the Raman excitation wavelength is tuned to match the energy of any electronic transitions of a system. Stimulated Raman scattering (SRS) was first discovered when a cell with nitrobenzene was introduced inside a ruby laser cavity. Woodbury and Ng observed a rather strong emission at the wavelength other than the fundamental wavelength (694.3 nm) of a ruby laser. The work of Stoicheff measured the various regions in Raman processes at different laser pump intensities of first Stokes in nitrogen and oxygen liquids, namely, SR, SRS, and saturation as the pump intensity grew. Several researchers have demonstrated different Raman gain from transient to transient depending on the pulse duration and vibrational lifetime under picosecond (ps) pulses. In the early 1970's, the white light continuum spanning the visible and part of NIR, now called supercontinuum (SC), was discovered by Alfano and Shapiro [1] in solids and liquids using ps pulses. The use of SR loss and gain is active for imaging biological materials such as brain for SRS microscopes.

This part reports for the first time on novel nonlinear optical process on the observation of Resonant Stimulated Raman Scattering (RSRS) process for improving/enhancing imaging using resonant process which was found in a solution of β-carotene in methanol using pump beam at the second harmonic generation (SHG) from a Q-switched Nd:YAG laser. RSRS combines both RRS and SRS nonlinear processes. The RSRS observed effect is attributed arising in part from cubic from quartic anharmonic vibrational interactions among solute carotene in resonance with solvent methanol vibrational modes.

The discovery of RSRS is important towards improving over conventional SRS microscopy for imaging vibrational states of cancer, and the applications of this technique in the areas of neuroscience, cancer, and biomedicine.

In SRS microscopy, the sample is coherently driven by two lasers: one is the pump beam with frequency $\omega_L$ and the other is the Stokes beam with frequency $\omega_s$, where the difference is equal to a particular Raman-active molecular vibration of the sample. The SRS signals, including both stimulated Raman loss (SRL) at the laser pump beam and stimulated Raman gain (SRG) at the Stokes beam are generated due to the nonlinear interaction between the photons and the vibration of the molecules for imaging. The development of novel nonlinear vibrational spectroscopies has allowed broadband SRS to provide high intensity with low fluorescence background free coherent signal. In SRS, the sample is interrogated by a pair of overlapped narrow-band ps Raman pulses and/or broadband femtosecond (fs) probe pulses. In SRS G/L process the vibrational spectra occurs with the incoherent fluorescence background and electronic susceptibility $\chi_3$ is efficiently suppressed.

Background Theory on SRS SC Microscope

The intensity of the spontaneous Raman (SR) is weak ($10^{-6} I_L$), where $I_L$ is the laser intensity. The power scattered is given by $$P_s = N\left(\frac{\partial \sigma}{\partial \Omega}\right)_R \Delta\Omega I_L = N\sigma_R I_L, \qquad (7)$$

where cross-section $\sigma_R$ is given by:

$$\sigma_R = \left(\frac{\partial \sigma}{\partial \Omega}\right)_R d\Omega, \qquad (8)$$

and N is the number of molecules in the observed volume and $$\left(\frac{\partial \sigma}{\partial \Omega}\right)$$

is the differential Raman cross-section.

When the excited laser wavelength approaches an electronic absorption in a material, the transitions among the states go from virtual to real. The Raman scattering signal becomes enhanced due to the resonant effect. Thus, enhancement arises from the cross section from the energy denominator of nonlinear susceptibility becoming small as the laser frequency matches the electronic energy states. The virtual transition of the intermediate state becomes real and Raman effect becomes larger by 10 to 1000 folds depending on how close the laser photon energy is in the transit from the ground state (i) to electronic state j. They are in resonances and out of resonances with the pump and Raman shifted light with the electronic states. This process is called Resonance Raman scattering (RRS).

The Raman cross-section for single molecule is given by:

$$\sigma_R = \left| \sum \frac{A_{iijf}}{(\omega_{ij} - \omega_L - i\Gamma_j)} + \frac{A_{jijf}}{(\omega_{jf} - \omega_L - i\Gamma_j)} \right|^2 \quad (9)$$

for in and out resonances, so when $\omega_L$ approaches $\omega_{ij}$, the denominator—reduces and $\sigma$ increases and Raman becomes resonant Raman scattering RRS. The frequency dependence cross section in Eq. 9 shows the salient resonance features between the pump and probe frequency with electronic absorption for enhancement.

When an intense laser pulse (ns, ps, fs) enters a material, the Raman effect occurs. The light is first scattered over a large angle $\Omega$. As the Raman light travels with the pump laser in the forward and backward directions it can become larger than the Raman light traveling out of the beam at other angles as it propagates with laser pulse and over a length of more than 10 cm. Depending upon the intensity of the laser pump pulse the Raman light in the forward and backward directions can become so large that it is stimulated and becomes laser-like with high direction and coherence.

The intensity of Raman Stokes is given by a Beer-Lambert's law-like equation:

$$I_{RS}(z) = I_{RS}(0)\exp(Gz - \alpha z), \quad (10)$$

where G is the gain, $\alpha$ is the loss, and $I_{RS}(0)$ is initial Stokes from zero point fluctuation which has SR at z=0. In any SRS, the Raman gain must exceed the loss due to absorption in the media, where Gz>25 and the medium will experience an exponential growth of photon at Stokes frequency. The Raman light in the forward direction becomes much greater than spontaneous Raman and becomes SRS with about 1% to 10% of energy transferred from pump frequency.

The Raman gain G is:

$$G = N\left(\frac{\partial \sigma}{\partial \Omega}\right) I_L \Delta \Omega \quad (11)$$

Carotene was selected as an ideal test solute to demonstrate RSRS in biomedical media in solution. Carotene is synthesized in plants and animals. It is a chromophore in carrots, tomatoes, and in skin, and is known for its orange color. In humans, carotene is involved in antioxidant processes and defense mechanisms. In this research observation, carotene provides the methanol solution with the necessary enhancement of cross-section in the visible where the absorption peaks at 450 nm extending out to 532 nm. The main absorption of carotene is from $S_2$ state since $S_1$ is dipole forbidden.

The focus here is to state the first observation of Resonant Stimulated Raman scattering (RSRS) in a solution of β-carotene in methanol using pump SHG from Q-switched Nd Laser of 5 ns at 532 nm laser beam. RSRS combines both RRS and SRS processes a first new non-linear optical (NLO) effect. The observation of RSRS is most important for new Stimulated Raman Loss (SRL) and Stimulated Raman Gain (SRG) microscopes in order to enhance signals of images from vibrations in biomedical tissues, cells and chemicals in samples. The selection of the pump or Stokes near an electronic resonance will improve the signal to noise ratio (i.e., S/N) of the SRS microscope image. Part of SC spectrum can be used to achieve resonance in the material spectra for RSRS, see FIG. 6.

The key observation is that the carotene solute influences the vibrations of methanol. The solute-solvent system can have different interactions: vibrations between solute molecules, solvent molecules, or between solute and solvent. There is a coupling as shown in spontaneous Raman at 2834 $cm^{-1}$. Anharmonic coupling between solute and solvent from solvation of shells account for the relaxation of an excited solvent and solute molecules. The conservation of energy affect the relaxation of a vibration. If there is no energy match the vibration is long, and if the vibration matches among the vibrations decay is fast. In Fermi Golden rule the rate among states of interaction is from square of Hamiltonian from anharmonic terms from potential $V_n$ where n>3, and the density of final states ρ is available. The latter term ρ is main process to determine the system process from solute—solvent, solvent, and solute states. The anharmonic coupling allows for the flow of energy among the vibrational modes. A cubic anharmonicity allows for excitation of the solute and solvent vibrations modes to be exchange during interaction. A quartic anharmonicity would exchange correspond to vibration and bath phonon exchange, such as 2 vibrations from solute and solvent and a phonon bath.

Vibrational energy processes in binary solvent A and solute B system can have cubic and quartic interactions. A possible quartic interaction to excite the 2834 $cm^{-1}$ in methanol solvent from resonance Raman of carotene is the 1525 $cm^{-1}$ and 1157 $cm^{-1}$ modes can generate 2834 $cm^{-1}$ and deactivate 150 $cm^{-1}$ methanol bath phonons such as 1525 $cm^{-1}$+1157 $cm^{-1}$→2834 $cm^{-1}$−150 $cm^{-1}$ [A*A*B*B—goes to AABB*]. A possible model where upon excitation by 532 nm, the carotene undergoes RR scattering at 1525 $cm^{-1}$ and 1157 $cm^{-1}$ than transfer energy to methanol with bath phonons from methanol to excite the 2834 $cm^{-1}$ of methanol mode.

Kasier group investigated cubic interactions, one excited molecule say A* decays though resonant and non-resonance interaction in trinary collisions: A*AA, A*AB, and A*BB. To affect the vibration lifetime decay, Kaiser and coworkers observed the triple interaction of higher vibration $CH_3$ with addition of another liquid of $CCl_4$. The vibration lifetime of A* of $CH_3$ increase with more of B. Therefore the Raman gain will become larger with addition of $CCl_4$ going from transient gain to steady state gain. Raman gain will increase towards more steady—state—like when lifetime of the vibrations becomes longer. This effect will be more important using femtosecond and picosecond pulses, not nanosecond pump laser pulse. So in this study the resonance of B (i.e., carotene) to A (i.e., methanol) will be major cause for RSRS process.

The solute carotene affects the vibrations (1525 $cm^{-1}$+ 1152 $cm^-$) transfer of the resonance to solvent methanol (M) (2834 $cm^{-1}$ and phonon bath) in a quartic interaction (C1*C2*M1*M2), thereby enhancing the cross section. A theoretical analysis following on the underlying physics is needed to explain the RSRS process observed vibrations of solute carotene and solvent methanol. Time resolved femtosecond pump probe is in order to test and determine the energy transfer speculative mechanism.

Streak Camera Time Resolved Microscope

Using the short pulse associated with SC allows for Time resolved imaging to yield temporal properties of biomaterials and condensed matter imaging. Light propagating in turbid media such as tissue undergoes scattering which can blur images. The signal (light intensity) is governed and defined by key parameters for tissue: the scattering coefficient $\mu_s$, the transport coefficient $\mu_s'$, the absorption coefficient $\mu_a$, and the mean cosine scattering angle parameter g. These are a function of wavelength ($\lambda$). From $\mu_s$ and $\mu_s'$, the mean cosine scattering angle parameter g can be obtained directly from time resolved measurements of the transmission and backscatter using a Streak Camera to measure transmitted or reflected signal form a point xyz in the sample 1 (t, xy).

One can create a map on sample at xyz and extract the $\mu_s'$ from the tail in time. The light transport is made up of ballistic and diffusive components, see Ref 4. The ballistic light can provide high quality images, reveal hidden objects in turbid media and is represented by $\mu_s$ and $\mu_a$. The transport theory of diffuse light intensity is represented by the diffuse equation $$\frac{\partial I(r,t)}{\partial t} = \nabla (D \nabla I(r,t)) - v\mu_a I(r,t) + q^{(0)}(r,t) \quad (12)$$

where $q^{(0)}(r,t)=\delta(r)\delta(t)$ is the incident source, r is the position, v is the speed of light, and D is the diffusion coefficient, given by $$D = \frac{v}{3\mu_s(1-g)} \quad (13)$$

where $\mu_s'=\mu_s(1-g)$ and $$\mu_s' = \frac{1}{Ltr.}$$

The value of $\mu_s'$ is extracted from D in Eq. 14. Similarly, as shown by Yoo [4] in the case of a slab sample, the transport theory of diffuse light intensity can be described by $$I_z(t) = \frac{1}{4d^2 t} \sum_{m=1}^{\infty} m \sin\left(\frac{m\pi z}{d}\right) \exp\left[-Dt\left(\frac{m\pi}{d}\right)^2\right] \exp\left(\frac{-vt}{l_a}\right) \quad (14)$$

where $d=z+2z_0$, $z_0=0.71/t$ and where $z_0$ is the extrapolation length and z is the thickness of the sample. Thus, the transport length $1/\mu_s'$ and the absorption length $L_a$ can be approximated, along with temporal information, using these equations (see Ref 4) at each point in the tissue to map out these values for different parts of brain and for cancer and non cancer region.

The streak camera, the heart of the time-resolved SC microscope, allows for direct measurement of $\mu_s'(\lambda)$ from the temporal profile. Using a 100 fs pulsed Ti: Sapphire laser or SC laser at select wavelengths around the first NIR optical window (from 700 nm to 1100 nm) and a microscope objective of >10 to 20 X, $\mu_s'(\lambda)$ can be obtained in space at different sites in the brain, skin and breast tissues. 3D maps of $\mu_s'$ from tissue slices will be acquired. One can develop 5D image maps of tissue using space (3D), time t, and wavelength $\lambda$.

The full potential of SC time-resolved measurements is taught. One can form a Streak Cameras with 5 to 10 ps resolution imaging system to get $\mu_s'(\lambda)$ at xyz of tissues and biomaterials. The spatial location of an abnormality in a scattering medium such as the brain or the breast using the time behavior of the scattered light through turbid media may be a valuable noninvasive tool for Streak Camera microscope.

REFERENCES

1. R. R. Alfano and S L Shapiro, Phys. Rev. Lett. 24, 592-594, 584-587, 1219-1222 (1970).
2. R. R. Alfano and S. L. Shapiro, Chem. Phys. Lett. 8, 631-633 (1971).
3. R. R. Alfano U.S. Pat. No. 9,414,887 B2, 2016.
4. K. M. Yoo, F. Liu, and R. R. Alfano, Phys. Rev. Lett. 64, 2647 (1990).

The invention claimed is:

1. Imaging apparatus comprising a microscope; a source of supercontinuum (SC) light, said microscope comprising an objective lens; optical narrow and wide band filters to provide SC pump and probe laser wavelengths configured to direct through said objective lens to a sample to be imaged having a scattering transport coefficient $\mu_s'$; an optical detector; an optical splitter configured for directing said SC light towards a sample and directing the SC light reflected from the sample including linear and non-linear light components representative of the sample to said optical detector; imaging means for converting an output of said optical detector including said linear and non-linear components into signals corresponding to said linear and non-linear components utilizing at least one of electronic and vibrational resonances through said microscope; and a streak camera for time resolve data from a sample; and an XYZ scanner for scanning said SC light in selected ones of X, Y and Z directions prior to directing said SC light into said microscope for creation of 2D xy image slices at depth z and 3D by adding up z slices from 2D planes and time adds to 4D and wavelength from SC give 5D maps with $\mu_s'$.

2. Imaging apparatus comprising a microscope; a source of supercontinuum (SC) light, said microscope comprising an objective lens; optical narrow and wide band filters to provide SC pump and probe laser wavelengths configured to direct through said objective lens to a sample to be imaged having a scattering transport coefficient $\mu_s'$; an optical detector; an optical splitter configured for directing said SC light towards a sample and directing the SC light reflected from the sample including linear and non-linear light components representative of the sample to said optical detector; imaging means for converting an output of said optical detector including said linear and non-linear components into linear and non-linear signals utilizing at least one of electronic and vibrational resonances through said microscope, wherein said microscope is configured to image 5D tomography images: space (xyz), time (t) and wavelength ($\lambda$) maps of tissue wherein time resolved the transport scattering length $L_{tr}=1/\mu'_s$ at xy position at z for give wavelength, $\lambda$ of SC for an image map of tissue obtained from I(t) scattered profile in time, where I(t) is the intensity of the signals as a function of time.

* * * * *